United States Patent
Nakamura

(10) Patent No.: US 9,278,204 B2
(45) Date of Patent: Mar. 8, 2016

(54) PRESSURIZED GAS MIST BATHING SYSTEM

(75) Inventor: Shoichi Nakamura, Nagano (JP)

(73) Assignees: ACP JAPAN CO., LTD., Tokyo (JP); Shoichi Nakamura, Higashichikuma-gun, Nagano (JP)

( * ) Notice: Subject to any disclaimer, the term of this patent is extended or adjusted under 35 U.S.C. 154(b) by 327 days.

(21) Appl. No.: 13/884,474

(22) PCT Filed: Jan. 20, 2012

(86) PCT No.: PCT/JP2012/051249
§ 371 (c)(1),
(2), (4) Date: May 9, 2013

(87) PCT Pub. No.: WO2012/099252
PCT Pub. Date: Jul. 26, 2012

(65) Prior Publication Data
US 2013/0226076 A1 Aug. 29, 2013

(30) Foreign Application Priority Data

Jan. 21, 2011 (JP) ................. 2011-010648

(51) Int. Cl.
| | |
|---|---|
| *A61M 37/00* | (2006.01) |
| *A61H 33/14* | (2006.01) |
| *A61M 35/00* | (2006.01) |
| *A61M 1/00* | (2006.01) |
| *A61M 27/00* | (2006.01) |

(52) U.S. Cl.
CPC ............ *A61M 37/00* (2013.01); *A61H 33/14* (2013.01); *A61H 2033/143* (2013.01); *A61H 2033/145* (2013.01); *A61H 2201/0207* (2013.01); *A61H 2201/105* (2013.01); *A61H 2201/165* (2013.01); *A61H 2201/1619* (2013.01); *A61H 2201/1635* (2013.01); *A61H 2201/1642* (2013.01);

(Continued)

(58) Field of Classification Search
CPC ....... A61M 35/00; A61M 1/00; A61M 27/00; A61F 13/00; A61F 13/02
See application file for complete search history.

(56) References Cited

U.S. PATENT DOCUMENTS 4,224,941 A * 9/1980 Stivala .......................... 604/23
5,263,476 A * 11/1993 Henson .................... 128/204.18

(Continued)

FOREIGN PATENT DOCUMENTS

| | | |
|---|---|---|
| JP | 2000-245841 A | 9/2000 |
| JP | 3163837 U | 10/2010 |
| WO | WO 2010/090210 A | 8/2010 |

*Primary Examiner* — Tatyana Zalukaeva
*Assistant Examiner* — Ilya Treyger
(74) *Attorney, Agent, or Firm* — Manabu Kanesaka

(57) ABSTRACT

The invention is to provide a pressurized gas mist bathing system, ensuring hygiene and reduction in costs, by making only one part of the system disposable. This system comprises a gas supply means 10; a gas mist generating means 30 which has a portion connecting the gas supply means 10, a liquid storage of storing a liquid, a nozzle, a liquid suction pipe of sending the liquid to the tip of the nozzle, a collision member of colliding the liquid blown up by a gas stream from the nozzle therewith, a cylindrical gas inlet supplied with the gas and leading the gas till the upper portion of the nozzle, and a donut-shaped gas mist outlet collecting and discharging the gas mist around the periphery of the gas inlet; and a pressurized living organism bathing cover 50 for covering the skin and the mucous membrane of a living organism and formed with a space for sealing inside the gas mist from the gas mist generating means; and in the gas mist generating means 30, at least the liquid storage is displaceable and replaced by another, so that liquid storage is made disposable.

19 Claims, 14 Drawing Sheets

Figure 1:
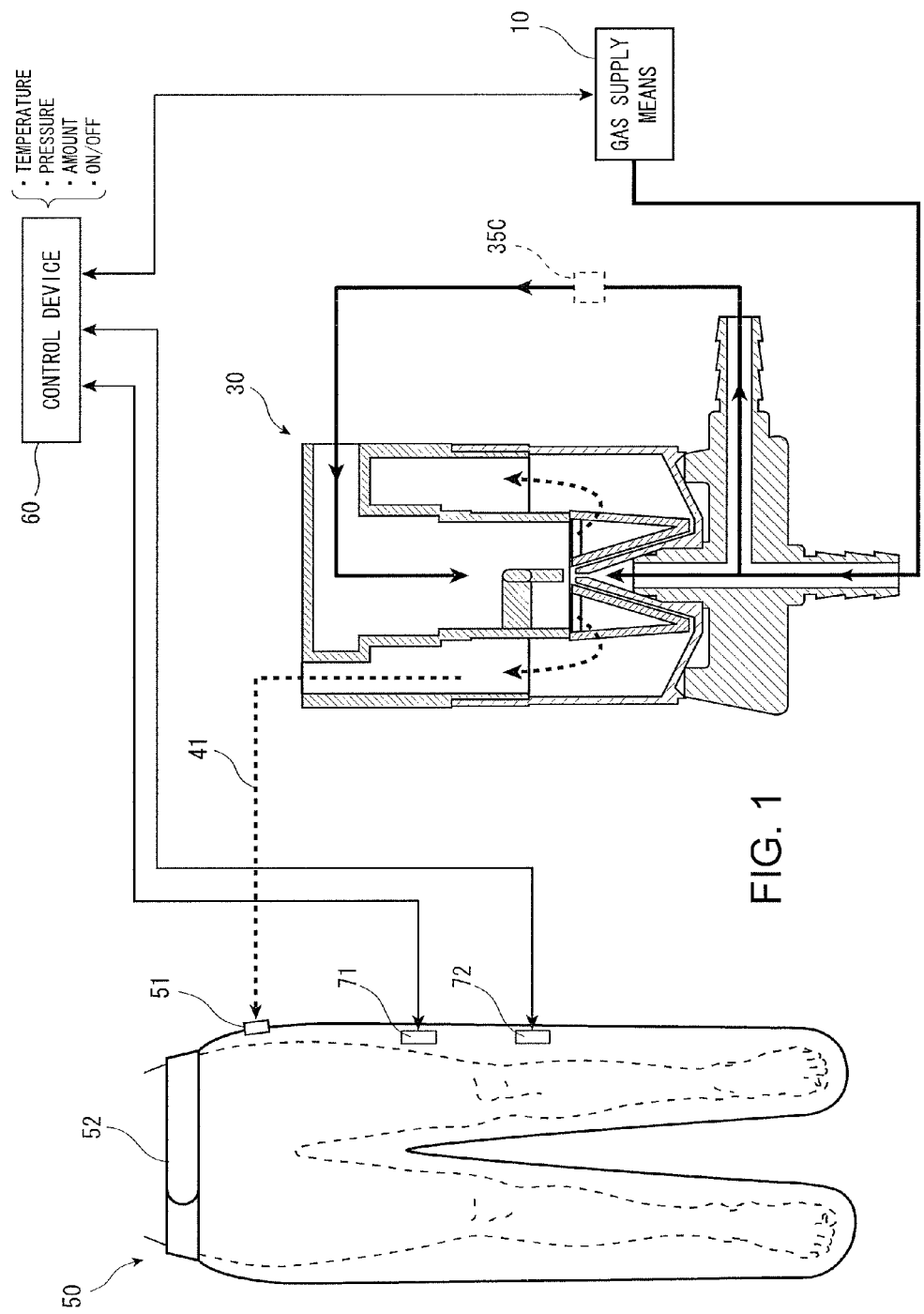

(52) U.S. Cl.
CPC . *A61H2201/1688* (2013.01); *A61H 2201/5007* (2013.01); *A61H 2201/5082* (2013.01); *A61H 2205/06* (2013.01); *A61H 2205/065* (2013.01); *A61H 2205/08* (2013.01); *A61H 2205/106* (2013.01); *A61H 2205/108* (2013.01); *A61H 2205/12* (2013.01)

(56) References Cited

U.S. PATENT DOCUMENTS 5,516,517 A * 5/1996 Gardner .................. 424/401
2002/0156416 A1 * 10/2002 Stenzler .................. 604/23

* cited by examiner

PRESSURIZED GAS MIST BATHING SYSTEM

RELATED APPLICATIONS

The present application is National Phase of International Application No. PCT/JP2012/051249 filed Jan. 20, 2012, and claims priority from Japanese Application No. 2011-010648, filed Jan. 21, 2011.

TECHNICAL FIELD

The present invention relates to a pressurized gas mist bathing system for improving absorption efficiency of gas from the skin or the mucous membrane of a living organism, in which a mist is prepared by pulverizing and dissolving a liquid of oxygen or carbon dioxide and a medicine, or a mixed gas of oxygen and carbon dioxide and the medicine, and the mist is caused to directly contact the skin and mucous membrane of the living organism at pressure of not less than a predetermined value.

BACKGROUND OF THE INVENTION

Conventionally, it has been known that carbon dioxide (carbonic acid anhydride: $CO_2$) has two properties of being not only soluble in water (water-soluble) but also soluble in fat (fat-soluble) and, owing to having both properties, when only contacting to the skin and the mucous membrane of the living organism which are like as mixed with water and fat, carbon dioxide penetrates under a subcutaneous tissue and expands blood vessels around the penetrated parts, and it works to improve the blood circulation. By this action of accelerating the blood circulation, it displays various physiological effects such as dropping of blood pressure, improving of metabolism or accelerating to remove pain substance or waste product. Further, it has also anti-inflammation and anti-bacterial function. Therefore, carbon dioxide has recently been given attentions also from viewpoints of improving health or beauty other than the purpose of medical cares.

In the tissue of the living organism, carbon dioxide works to release oxygen having been carried in combination with hemoglobin existing in a red blood cell. Around parts at the high concentration of carbon dioxide, the red blood cell releases more oxygen. Thus, supply of oxygen to cells by the red blood cell is mainly controlled by carbon dioxide. In short, being without carbon dioxide, hemoglobin remains as having been combined with oxygen and the cell becomes unable to receive oxygen. Carbon dioxide seems to be waste products resulted from action of the cell, however, as is seen, it plays in fact very important roles in the living organism.

Further, recently, oxygen of the high concentration has also widely been known as effective over activity of metabolism, acceleration of blood circulation, fatigue recovery, or stability of blood pressure. Other than them, oxygen has effects of disinfection or sterilization by oxidation.

Thereupon, an inventor of this invention has developed a pressurized gas mist bathing device and system, in which a medicine is dissolved efficiently in oxygen or carbon dioxide, and in addition to these gases, a physiological action of the medicine is given effectively to the living organism.

SUMMARY OF THE INVENTION

Problems that the Invention is to Solve

For ensuring hygiene of the pressurized gas mist bathing device as above mentioned, desirably, parts of generating the gas mist are made disposable. However, if disposable parts are large in size, a cost becomes high and futility increases.

In view of the above mentioned circumstances, it is an object of the invention to provide such a pressurized gas mist bathing system, only one part of which is made disposable for ensuring hygiene so that reduction in costs can be realized.

Means for Solving the Problems

For solving the above mentioned problems, the invention is to provide a pressurized gas mist bathing system, which causes a mist to contact the skin or the mucous membrane of a living organism, the mist (called as "gas mist" hereafter) having been prepared by pulverizing and dissolving carbon dioxide or oxygen and liquid, or a mixed gas (called as "gas" hereafter) of carbon dioxide and oxygen and liquid of concentration being not less than predetermined value, and which comprises a gas supply means; a gas mist generating means which has a connecting portion connected to the gas supply means, a liquid storage of storing a liquid, a nozzle to be supplied with gas, a liquid suction pipe of sending the liquid to the tip of the nozzle, a collision member of colliding the liquid blown up by a gas stream from the nozzle therewith, a cylindrical gas inlet supplied with the gas and leading the gas till the upper portion of the nozzle, and a donut-shaped gas mist outlet of collecting and discharging the gas mist; and a living organism cover for covering the skin or the mucous membrane of the living organism and formed with a space for sealing inside the gas mist from the gas mist generating means, and wherein the gas mist generating means is characterized in that at least the liquid storage is displaceable and replaced by another liquid storage.

By the way, the invention refers it as "pulverizing and dissolving" to pulverize the liquid into fine liquid drops, and cause to contact and mix with gas (oxygen or carbon dioxide, or the mixed gas of oxygen and carbon dioxide).

Herein, the pressurized gas mist bathing system of the invention is desirably further provided with sensors for detecting measured values of air pressure, temperature, concentrations of oxygen and carbon dioxide, moisture and others, and control means for controlling interiors of the living organism cover members based on the measured values of the sensors to be within ranges of the set values having been previously determined.

It is also sufficient to further equip a pressurizing means for pressurizing the interior of the living organism cover member. By the way, this pressurizing means communicates with the living organism cover member, and desirably consists of a hollow gas storage enabling to discharge the gas mist into the living organism cover member.

If the gas mist is supplied intermittently into the living organism cover member by the control means, the living organism cover member may be effected with interval pressurization. Otherwise, if the pressurization member intermittently discharges the gas mist into the living organism cover member, it is also sufficient to carry out the interval pressurization on the living organism cover member.

Herein, preferably, the gas mist generating means has an air hole for taking in outside air.

Next, it is best that the above mentioned liquid is any one or plural combination of water, ionic water, ozone water, physiological salt solution, purified water, or sterilized and purified water. And it is desirable to further contain any one or plural combination of menthol, vitamin E, vitamin C derivative, retinol, anesthetic agent, cyclodextrin, photo catalyst, complex of photo catalyst and apatite, hyaluronic acid, coenzyme Q10, seed oil, propolis, ethanol, chlorhexidine gluconate, amphoteric surface active agent, benzalkonium chloride, alkyl diamino etherglycine acetate, sodium hypo-chlorite, peracetic acid, sodium sesquicarbonate, silica, povidone-iodine, sodium hydrogen carbonate, carbonate spring agent of high concentration, anti-allergic agent, anti-inflammatory agent, anti-febrile agent, anti-fungus agent, anti-influenza virus agent, influenza vaccine, steroid agent, anti-cancer agent, anti-hypertensive agent, cosmetic, or trichogen.

A size of the mist supplied from the gas mist generating means into the living organism cover member is suitably not larger than 10 μm.

The control means preferably holds pressure at 1.02 to 2.5 air pressure within the living organism cover member when taking the pressurized gas mist bath.

Further on, there may be provided an electric charge supply means for supplying charge to the mist from the gas mist supply means. At this time, the charge is preferably minus.

Desirably, the gas mist generating means has a gas mist supply pipe for supplying the gas mist into the pressurized living organism covering member, and this gas mist supply pipe is furnished with a filter for removing liquid drops attaching to the inside of the pipe. Still further, the gas mist supply pipe is suitably composed of a cornice shaped pipe over a whole or at one part of the gas mist supply pipe. In addition, this gas mist supply pipe is provided with a check valve.

The living organism member is also desirably furnished with the check valve at the gas mist supply port. By the way, it is suitable that the control means stops the gas supply from the gas supply means when the pressure value becomes more than the predetermined value.

The removable part of the gas mist generating means is in advance desirably sterilized.

Effects of the Invention

According to the pressurized gas mist bathing system of the invention, by making replaceable the liquid storage of storing medicines in the gas mist generating means for enabling to replace with another liquid storage, it enables to pay attention to hygiene together with reduction in costs.

BRIEF DESCRIPTION OF THE DRAWINGS

[FIG. 1] A generally schematic view of the pressurized gas mist bathing system in dependence on the first embodiment of the invention;

[FIG. 2] A typical and cross sectional view showing the gas mist generator of the pressurized gas mist bathing system of FIG. 1;

[FIG. 3] A perspective view, partially in section, of the generator main body in the pressurized gas mist bathing system shown in FIG. 1;

[FIGS. 4A and 4B] Typical cross sectional views showing embodiments of sealing the generator main body in the pressurized gas mist bathing system in FIG. 1;

[FIG. 5] A perspective view under a condition of looking the cover part member from the lower part in the pressurized gas mist bathing system shown in FIG. 1,

[FIG. 6] A partially enlarged cross sectional view of the generator main body in the pressurized gas mist bathing system in FIG. 1;

[FIG. 7] A typical view showing an example of connecting the gas mist generator and the pressurized gas mist bathing cover of the invention;

[FIG. 8] A typical view showing a configuration example (No. 1) of the pressuring cover for the living organism in the pressurized gas mist bathing system in dependence on the first embodiment of the invention;

[FIGS. 9A-9D] Typical views showing configuration examples (No. 2) of the pressuring covers for the living organism in the pressurized gas mist bathing system in dependence on the first embodiment of the invention;

[FIGS. 10A-10B] Typical views showing a configuration example (No. 3) of the pressuring cover for the living organism in the pressurized gas mist bathing system in dependence on the first embodiment of the invention;

[FIG. 11] A generally schematic view of the pressurized gas mist bathing system in dependence on a second embodiment of the invention;

[FIGS. 12A-12C] Typical views showing configuration examples (No. 1) of the pressurizing covers for the living organism in the pressurized gas mist bathing system in dependence on the second embodiment of the invention;

[FIGS. 13A-13B] Typical views showing a configuration example (No. 2) of the pressuring cover for the living organism in the pressurized gas mist bathing system in dependence on the second embodiment of the invention; and

[FIG. 14] A generally schematic view of the pressurized gas mist bathing system in dependence on a third embodiment of the invention.

EMBODIMENTS FOR PRACTICING THE INVENTION

In the following description, explanations will be made to embodiments of this invention, referring to the attached drawings.

[First Embodiment]

FIG. 1 is the generally schematic view of the pressurized gas mist bathing system in dependence on the first embodiment of this invention. As shown in FIG. 1, the pressurized gas mist bathing system of the present embodiment comprises a gas supply means 10 for supplying oxygen, carbon dioxide, or the mixed gas (called briefly as "gas" hereafter) of oxygen and carbon dioxide, a gas mist generator 30 serving as a gas mist generating means, and a pressurized living organism bathing cover 50 serving as a living organism covering means for sealing therein the supplied gas mist, and a control device 60 serving as a controlling means.

The gas supply means 10 supplies gas to a nozzle 33 and a gas inlet 37 of a later mentioned gas mist generator 30. The gas supply means 10 is provided with a regulator for adjusting pressure of gas, though not illustrated. There may be equipped a heater for heating gas and a temperature gauge for controlling temperature.

By the way, herein illustrated is an example of one gas supply means 10 supplying gas to both of the nozzle 33 and the gas inlet 37 of the gas mist generator 30, and it is also enough to furnish a plurality of gas supply Means 10 for supplying gas to the nozzle 33 and the gas inlet 37 from respectively different gas supply means 10. At this time, gases to be supplied may be different or the same.

The gas mist generator 30 stores previously the liquid therein, generates the gas mist made by pulverizing and dissolving the liquid and gas by high speed flow of gas supplied from the gas supply means 10, and supplies this gas mist into the pressurized living organism bathing cover 50. FIG. 2 is the cross sectional and typical view showing the structure of the gas mist generator 30. As shown in FIG. 2, the gas mist generator 30 is composed with a generator main body 31, a gas supply means connecting portion 35 and a cover part 46.

FIG. 3 is the perspective view, partially in section, of the generator main body 31. As shown in FIG. 3, the generator main body 31 is provided with a liquid storage 32 for storing the liquid, a nozzle 33 of discharging the gas supplied from the gas supply means 10, from a point open 33A, and a liquid suction pipe 34 of sucking up the liquid stored in the liquid storage 32 until the front end of the nozzle 33.

Figure 2:
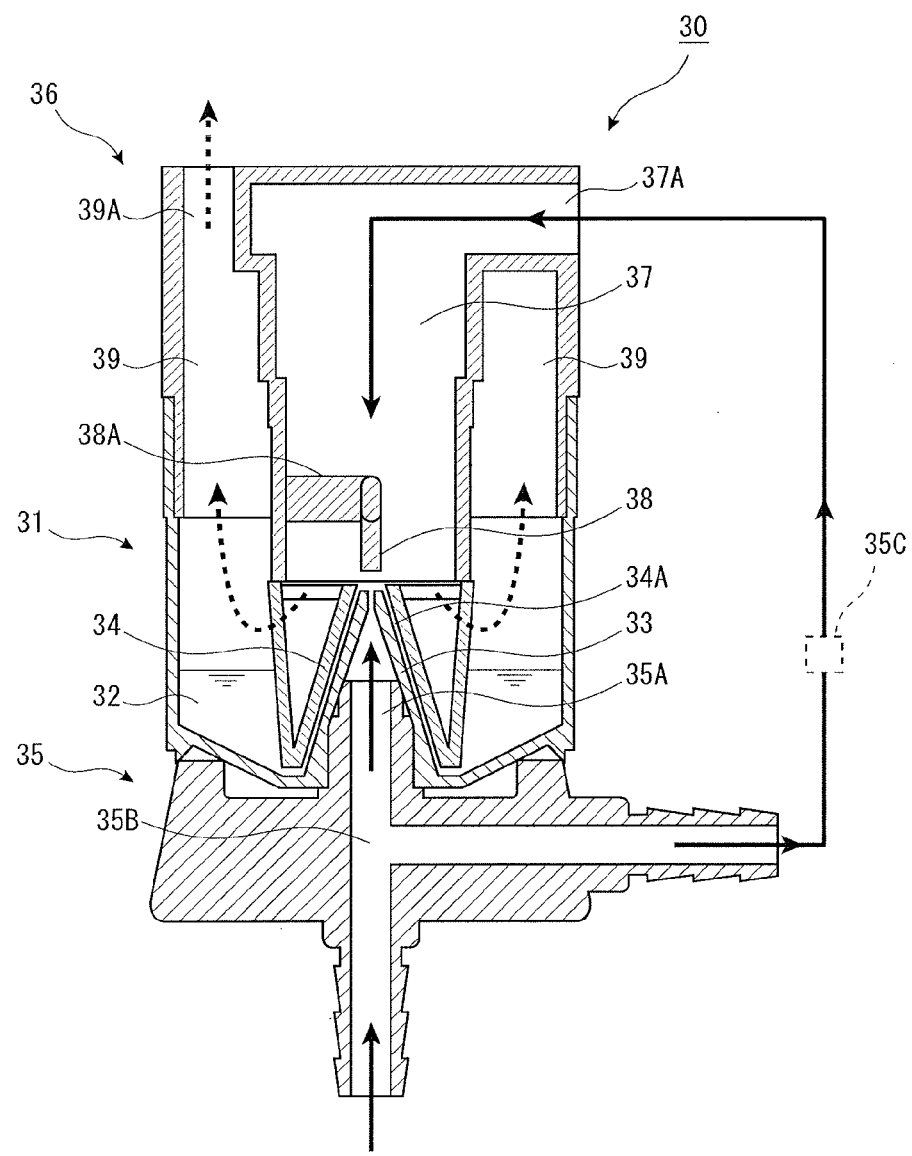
Figure 3:
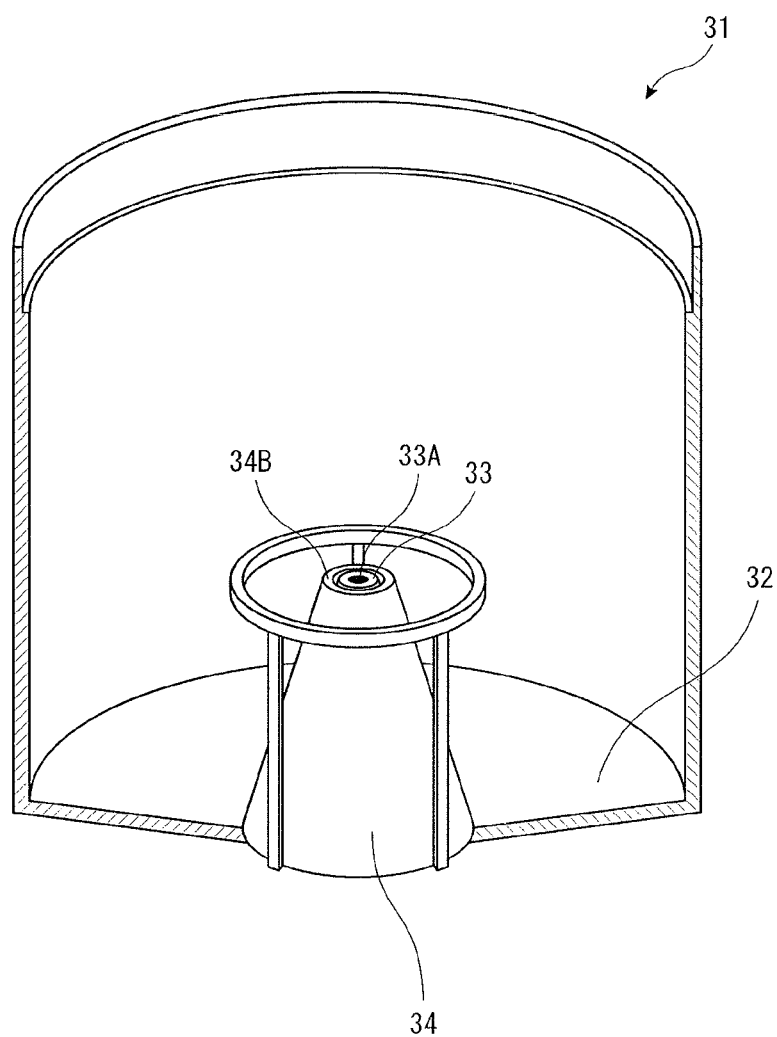
Figure 4A:
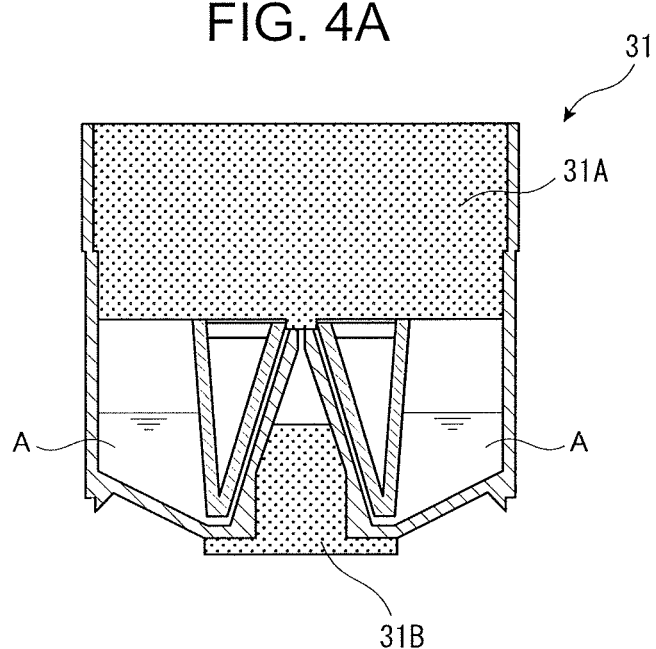
Figure 4B:
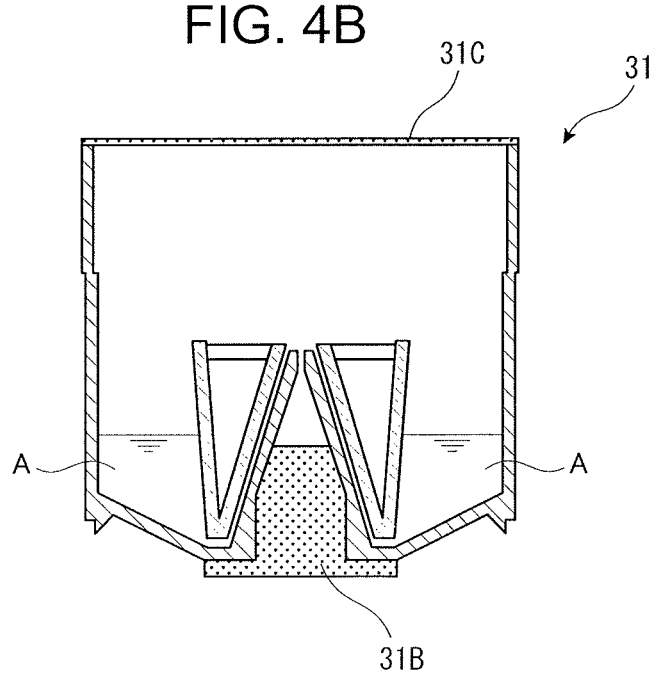

The liquid storage 32 is, as shown in FIGS. 2 and 3, formed with the inside of the bottom of the generator main body 31 and the inside of one part of its side wall. This liquid storage 32 is stored with a predetermined liquid previously when building a setting-up stage of this system. Under conditions of having stored the liquid, the generator main body 31 is sealed as shown in FIGS. 4A-4B. FIGS. 4A-4B are the typical views showing the embodiments of sealing the generator main body 31. FIG. 4A shows an example of sealing the generator main body 31 at its upper and lower parts with plugs 31A, 31B made of elastic members such as a rubber. FIG. 4B shows an example of sealing the generator main body 31 at its upper part with a film 31C made of an aluminum or a plastic by heating or an adhesive, and sealing the generator main body 31 at its lower part with a plug 31B made of an elastic member as a rubber.

Thus, the invention makes the at least liquid storage 32 removable in the gas mist generator 30 for replacing it with another new liquid storage 32 so that disposable parts are made less for restraining costs. Further, the generator main body 31 is offered as having been sealed, and by making disposable at any time, hygiene can be thus maintained. In particular, since the invention makes the liquid storage 32 disposable and can exchange it with a new liquid storage 32, it is possible to omit a structure of supplying the liquid such as medicines into the liquid storage 32, and realize reduction in size and in cost. By the way, this removable generator main body 31 is preferably sterilized in a manufacturing stage. Further, non-displaceable parts are also dealt with sterilization treatment prior to use.

Herein, for the liquid stored in the liquid storage 42, it is preferable to employ water, ionic water, ozone water physiological salt solution, purified water or sterilized and purified water. Further, these liquids are sufficient to contain medicines useful to users' diseases or symptom. As the medicines, for example, listed are anti-allergic agent, anti-inflammatory agent, anti-febrile agent, anti-fungus agent, anti-influenza virus agent, influenza vaccine, steroid agent, anti-cancer agent, anti-hypertensive agent, cosmetic, or trichogen. Further, these liquids are further possible to generate synergistic effects by coupling with a gas physiological action with single or plurality of menthol having a cooling action; vitamin E accelerating circulation of the blood; vitamin C derivative easily to be absorbed to a skin tissue and having a skin beautifying effect; retinol normalizing a skin heratinizing action and protecting the mucous membrane; anesthetic agent moderating irritation to the mucous membrane; cyclodextrin removing odor; photocatalysis or a complex of photocatalysis and apatite having disinfection and anti-phlogistic; hyaluronic acid having excellent water holding capacity and a skin moisture retention effect; coenzyme Q10 activating cells and heightening immunization; a seed oil containing anti-oxidation and much nutrient; or propolis having anti-oxidation, anti-fungus, a anti-inflammatory agent, pain-killing, anesthetic, and immunity. Otherwise, the liquid may be added with ethanol, gluconic acid chlorohexizine, amphoteric surface active agent, benzalkonium chloride, alkyldiamino ether glycin acetate, sodium hypochlorite, acetyl hydroperoxide, sodium sesqui-carbonate, silica, povidone-iodine, sodium hydrogen carbonate. In addition, carbonate spring of high concentration may be added (examples of organic components are sulfate, carbonate, or sodium dichloroiso-cyanurate).

At the bottom center of the generator main body 31 (the liquid storage 32), the nozzle 33 is placed. This nozzle 33 upheaves from the bottom of the liquid storage 32, and is shaped to be almost a circular cone squeezed toward an upper side of the generator main body 31. The nozzle 33 is connected, at its base end, to a gas discharge pipe 35A of the gas supply means connecting portion 35 to enable to discharge gas from its point open 33A.

The liquid suction pipe 34A is formed between the outer circumference of the nozzle 33 and the liquid suction pipe forming member 34 of the almost circular cone being larger by one turn than the nozzle 33. That is, as shown in FIG. 2, by positioning as covering the liquid suction pipe forming member 34 over the nozzle 33, the liquid suction pipe 34A is defined between the outer circumference of the nozzle 33 and the inner circumference of the liquid suction pipe forming member 34. Although having omitted to show, since a minute nail shaped projection is provided at a base end (the lower part of the almost circular cone part) of the liquid suction pipe forming member 34, a space is defined on the bottom between a base of the liquid suction pipe forming member 34 and the bottom of the liquid storage 32, and from this space, the liquid stored in the liquid storage 32 is sucked up by the liquid suction pipe 34A. In addition, the front end 34B of the liquid suction pipe forming member 34 opens nearly the point open 33A of the nozzle 33, and the liquid sucked up by the liquid suction pipe 34A collides with the gas flow discharged from the nozzle 33.

The gas supply means connecting portion 35 is a connecting portion with the gas supply means 10, and the gas flow from the gas supply means 10 is diverged into two branches (diverging part 35B in FIG. 2) within the gas supply means connecting portion 35, one being supplied to the nozzle 33 while the other being supplied to a later mentioned gas inlet 37.

Figure 5:
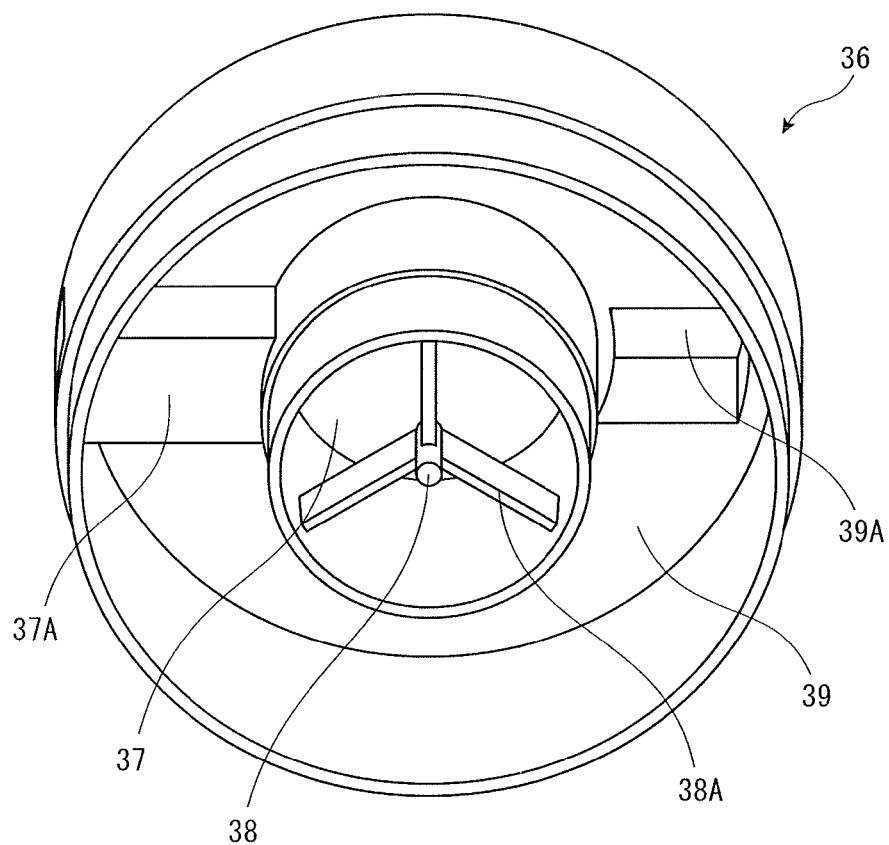

The cover 36 is a member which is attached on the upper part of the generator main body 31 and introduces the generated gas mist into the pressurized living organism bathing cover 50. Further, if supplying gas into the generator main body 31 independently of the nozzle 33, the member 36 heightens supplying pressure of the gas mist into the pressurized living organism bathing cover 50. Details of the cover 36 are shown in FIG. 5. FIG. 5 is the perspective view under the condition when looking the cover part 46 from its bottom side.

The cover part 36 has a gas inlet 37 which introduces gas into the generator main body 31 and makes air current for discharging the gas mist, a baffle (collision member) 38 disposed at a position in opposition to the point open 33A of the nozzle 33, and a gas mist outlet 39 which collects the gas mist and discharges into the pressurized living organism bathing cover 50.

The gas inlet 37 is a substantially L-shaped pipe hole for guiding gas from the outside of the cover part 36 until the periphery of the nozzle 33 of the generator main body 31, and the gas diverged by the gas supply means connecting portion 35 is supplied from this place into the generator main body 31. The gas inlet 37 is furnished on its upper part with a gas introducing mouth 37A connected via a tube or the like to the gas supply means connecting portion 35. The gas introducing mouth 37A may be furnished with an air hole for taking in outside air, though not illustrating here. It is sufficient to dispose a flow controller (for example, valve) 35C for controlling a gas supply amount to the gas inlet 37 as shown in FIGS. 1 and 2.

The baffle 38 is placed by a baffle supporter 38A in the vicinity of the lower end of the gas inlet 37. By the way, there is shown the example of the baffle 38 being secured to the cover part 36, but it may be disposed toward the side of the generator main body 31.

A gas mist outlet 39 is a donut shaped space formed around the cylindrical gas inlet 37 by the side and the upper part of the inside of the cover part 36. As having mentioned above, preferably, the gas inlet 37 is cylindrically shaped and the gas mist outlet 39 is donut-shape, but not necessarily limited thereto. Thus, by not partitioning but widening the space of the gas mist outlet 39, the mist can be smoothly discharged and prevented from liquefaction. Further, since the structure is simplified thereby, the cover 36 is heightened in washing efficiency and can be served hygienically.

The gas mist is generated owing to the nozzle 33 and baffle 38, and driven to the gas mist outlet 39 by gas from the gas inlet 37. The gas mist outlet 39 leads the gas mist to the pressurized living organism bathing cover 50. At the upper part of the gas mist outlet 39, there is provided a gas mist outlet 39A connected to the gas mist supply pipe 41 combining the gas mist generator 30 and the pressurized living organism bathing cover 50.

Figure 7:
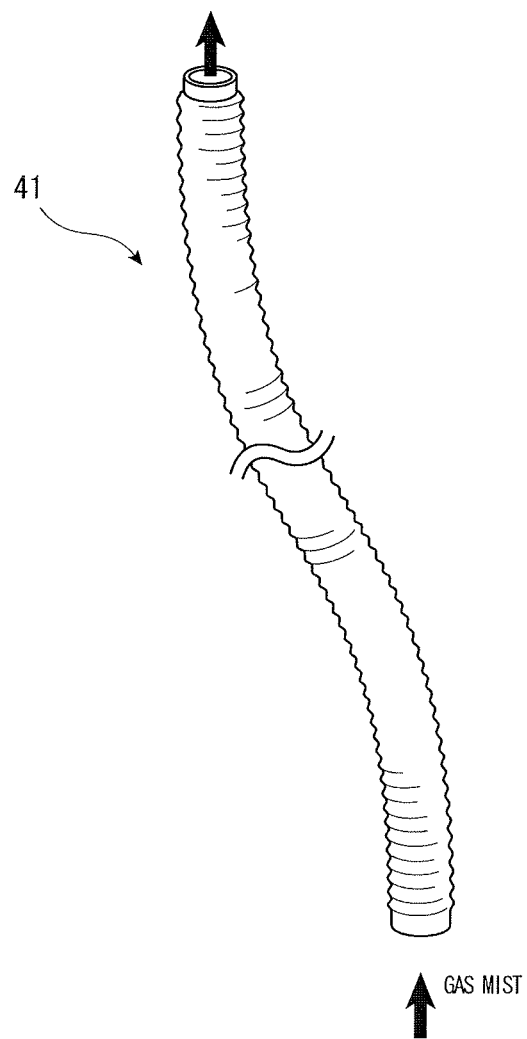

If the gas mist supply pipe 41 is composed wholly or partially with a cornice shaped and soft pipe of large diameter as shown in FIG. 7, it is freely bent and contracted so that the user's action is not limited. In addition, even if the gas mist flowing in the gas mist supply pipe 41 becomes liquefied, the cornice can remove the liquid owing to its concave and convex parts.

The gas mist supply pipe 41 is furnished at the inside with a check valve for preventing back flow of the gas mist. The gas mist supply pipe 41 may be provided with a filter for removing surplus liquid drops attached to the inside of the pipe, though not illustrated.

The pressurized living organism bathing cover 50 enables to form a space for covering the skin and mucous membrane of the living organism (herein, as the example, the lower extremity of the living organism) and to seal the gas mist inside. As an example, FIG. 1 shows a shape as trousers covering the lower extremity of the living organism. The pressurized living organism bathing cover 50 is composed of a pressure resistant, non-air permeable and non-moisture permeable material, for example, preferably, the natural rubber, silicone rubber, polyethylene, polypropylene, polyvinylidene chloride, poly-stylene, polyvinyl acetate, polyvinyl chloride, polyamide resin, poly-tetrafluoroethylene, and may be made of their multi-layers.

The pressurized living organism bathing cover 50 is connected to the gas mist supply pipe 41 and has the supply port 51 for introducing the gas mist inside. The supply port 51 is provided inside with the check valve to prevent from backflow of the gas mist. The pressurized living organism bathing cover 50 may have an open or a valve enabling to exhaust the gas mist for controlling inside pressure. The pressure control may be performed manually, but is desirably automatically based on measuring values of a later mentioned manometer 71 by a control device 60 together with supply or control of the gas mist. Further, a safety valve (by-pass valve) may be provided for automatically opening the valve when the inside of the pressurized bathing cover 50 becomes more than a constant pressure.

The pressurized living organism bathing cover 50 is inside installed with the manometer 71 for measuring internal pressure. The control device 60 controls generation or supply of the gas mist on the basis of measuring values of the manometer 71 for maintaining a pressure value within the pressurized living organism bathing cover 50 to be more than 1 air pressure (more preferably, around 1.02 to 2.5 air pressure). For example, supply of gas from the gas supply means 10 is controlled or stopped, otherwise, the gas mist from the pressurized living organism bathing cover 50 is exhausted. Further, the pressurized living organism bathing cover 50 is inside installed with a temperature gauge 72 for measuring temperature within the pressurized living organism bathing cover 50. The control device 60 performs "on-off" of a heater installed in the gas supply means 10 on the basis of measuring values of the temperature gauge 72 for maintaining a determined temperature (for example, around 38° C.) bringing about warm bath effects within the pressurized living organism bathing cover 50. As to others, the pressurized living organism bathing cover 50 may be installed inside with sensors for measuring concentrations of oxygen and carbon dioxide, moisture and others for controlling interiors of the cover based on the measured values to be within ranges of predetermined values by the control 60.

The pressurized living organism bathing cover 50 has, around its opening, a stopper 52 for attaching to and detaching from the living organism (herein, the lower extremity of the living organism) and for preventing leakage of the gas mist. The stopper 52 is suitably composed of, e.g., a face fastener of stretching property, or may have a sole string, rubber or their combination. For heightening a sealing property of the pressurized living organism bathing cover 50, the inside (such as an inside of the stopper 52) thereof may have a material attaching to the user's skin. The adhesive material is preferably, for example, a visco-elastic gel made of polyurethane or silicone rubber. Further this adhesive material is detachably used and exchangeable each time or if viscosity becomes weak.

The control device 60 is composed of a computer having CPU, memory and display. The gas pressure from the gas supply means 10, on-off switch of pressure, on-off switch of supply of the gas mist are performed for the pressurized gas mist bathing under the optimum condition. In particular, preferably, when the pressure value becomes more than a predetermined value in the pressurized living organism bathing cover 50, such a structure stops supplying the gas from the gas supply means 10 by the control device 60.

Next, reference will be made to one example of sequences taking the gas mist bathing by use of the pressurized gas mist bathing system of the above mentioned first embodiment.

At first, the sealed generator main body 31 is opened, the gas supply means connecting portion 35 and the cover 36 are set, and the gas mist generator 30 is accomplished. Subsequently, the gas supply means 10, the gas mist generator 30, the pressurized living organism bathing cover 50 and the control device 60 are connected, respectively. The pressurized living organism bathing cover 50 is fixedly secured to the living organism (herein, the lower extremity of the living organism) and closed. And the gas starts to supply from the gas supply means 10 into the gas mist generator 30.

Figure 6:
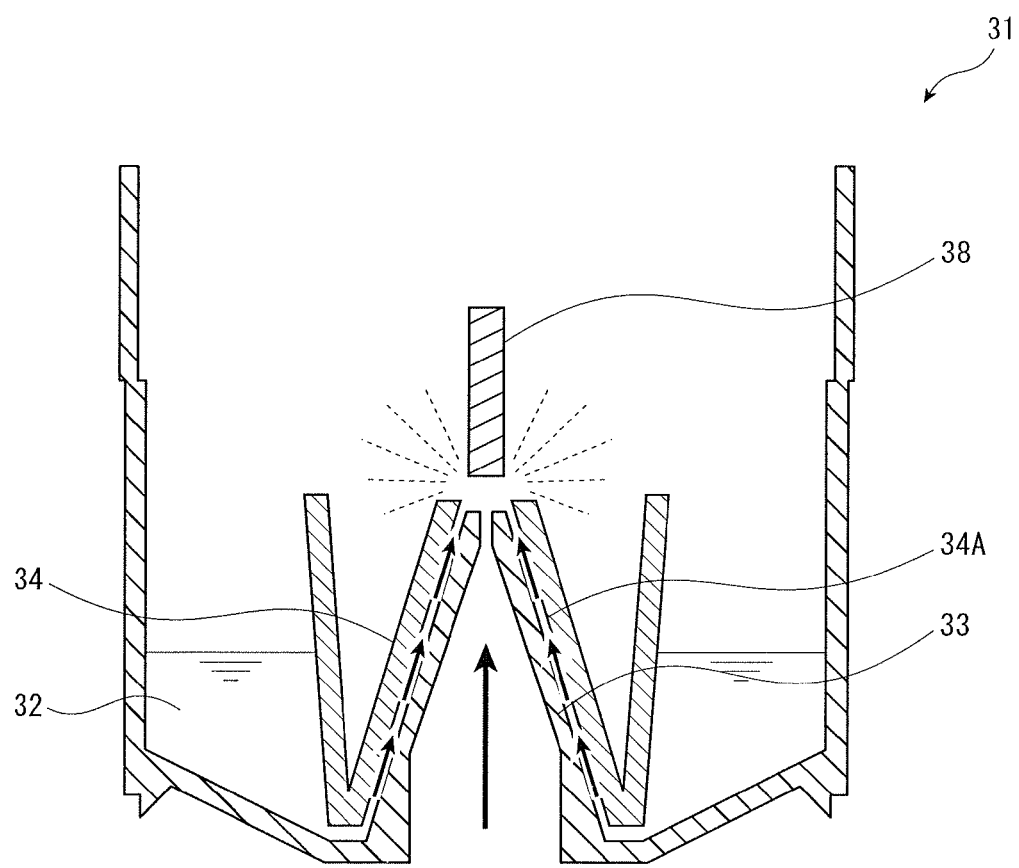

When the gas is supplied into the nozzle 33, since the nozzle 33 is, as shown in FIG. 6, reduced in diameter toward the front end, the gas increases flowing speed and is discharged. The liquid is sucked up from the liquid sucking pipe 34A by negative pressure generated owing to air current at this time, spouted up at the front end 34B of the liquid sucking pipe 34A and collides with the baffle 38, and the mist is generated by this collision. Desirably, diameter of the mist generated by this collision is fine, and concretely, less than 10 μm is optimum. The finely pulverized mist can display effects of minus ion.

The gas is further supplied also from the gas inlet 37 into the generator main body 31 to increase discharging pressure of the generated gas mist. During generating the gas mist, the control device 60 carries out adjustments of the supplying pressure or temperature of gas.

The generated gas mist is discharged into the pressurized living organism bathing cover 50 from the gas mist supply pipe 39 via the gas mist supply pipe 41. The control device 60 adjusts each of the means from the measuring values of the manometer 71 and the temperature gauge 72, such that the inside of the pressurized living organism bathing cover 50 is made optimum pressurized and heated condition (around 1.02 to 2.5 air pressure and around 38° C.), and under these conditions, the pressurized gas mist bathing is performed.

The above mentioned explanation has been made to the lower extremities of the human living organism as the example to be performed with the pressurized gas mist bathing, and the invention is applicable to various parts of the living organism. Then, the optimum pressurized gas mist bathing is performed by using the shapes of the pressurized living organism bathing cover 50 meeting object parts of the living organism.

Figure 8:
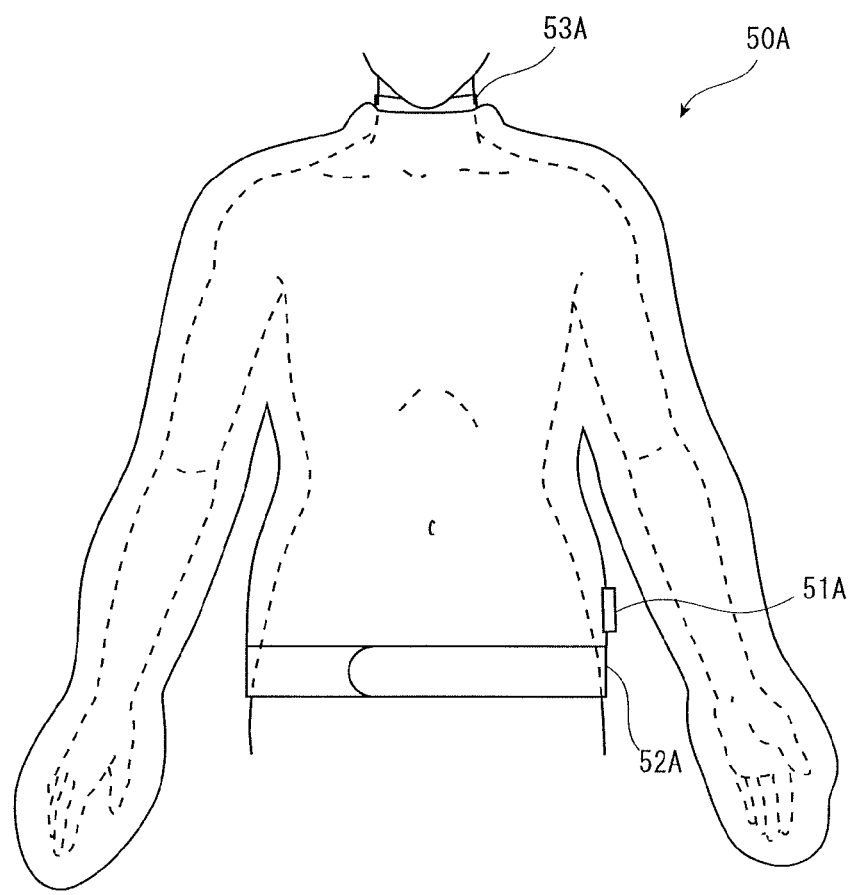

FIGS. 8 to 10 show the various shaped examples of the pressurized living organism bathing cover 50. At first, FIG. 8 shows the schematic view of the pressurized bathing cover 50A for the upper half of the living organism. The pressurized bathing cover 50A has a shape for wrapping the whole of the upper half of the living organism, and has a stopper 52A for attaching to and detaching from the living organism when opening a waist part and stopping leakage of the gas mist sealed inside. A stopper 53A is similarly formed around the opening of a neck. 51A designates a supply port for introducing inside the gas mist.

Figure 9A:
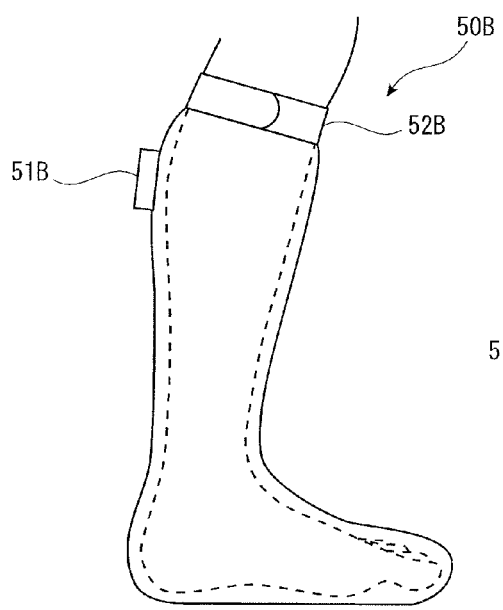
Figure 9B:
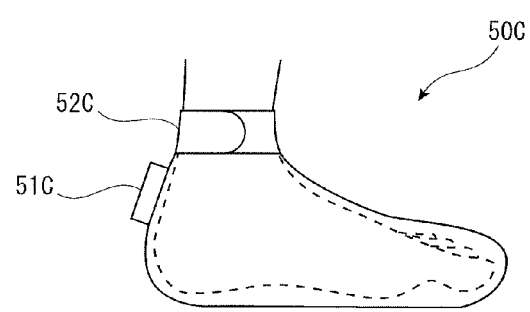
Figure 9C:
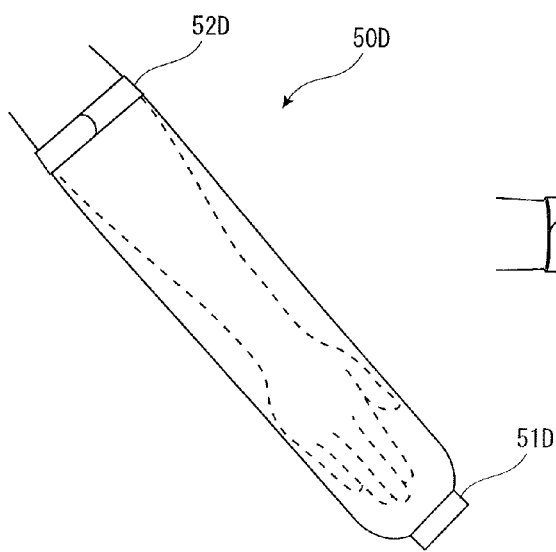
Figure 9D:
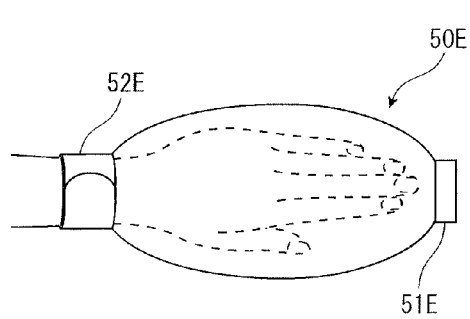

FIGS. 9A-9D show the variously shaped examples of the pressurized living organism bathing cover 50 for covering further limited parts of the living organism. FIG. 9A is a pressurized bathing cover 50B for one-side lower extremity (lower part under a knee) of the living organism. The pressurized bathing cover 50B has a stopper 52B at its opening part and a supply port 51B for introducing inside the gas mist. FIG. 9B is a pressurized bathing cover 50C for a foot. The pressurized bathing cover 50C has a stopper 52C at its opening part and a supply port 51C for introducing inside the gas mist. FIG. 9C is a pressurized living organism bathing cover 50D for a forearm. The pressurized bathing cover 50D has a stopper 52D at its opening part and a supply port 51D for introducing inside the gas mist. FIG. 9D is a pressurized living organism bathing cover 50E for a hand. The pressurized bathing cover 50E has a stopper 52E at its opening part and a supply port 51E for introducing the gas mist inside thereof.

Figure 10A:
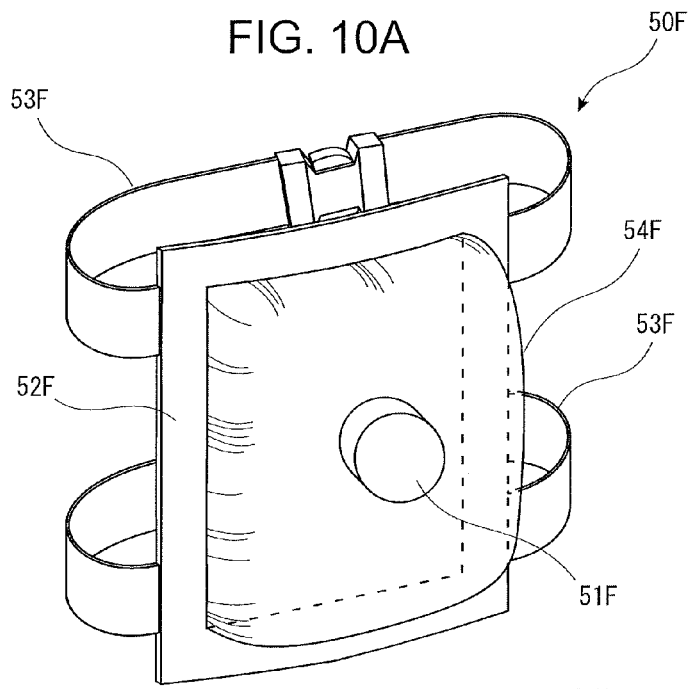
Figure 10B:
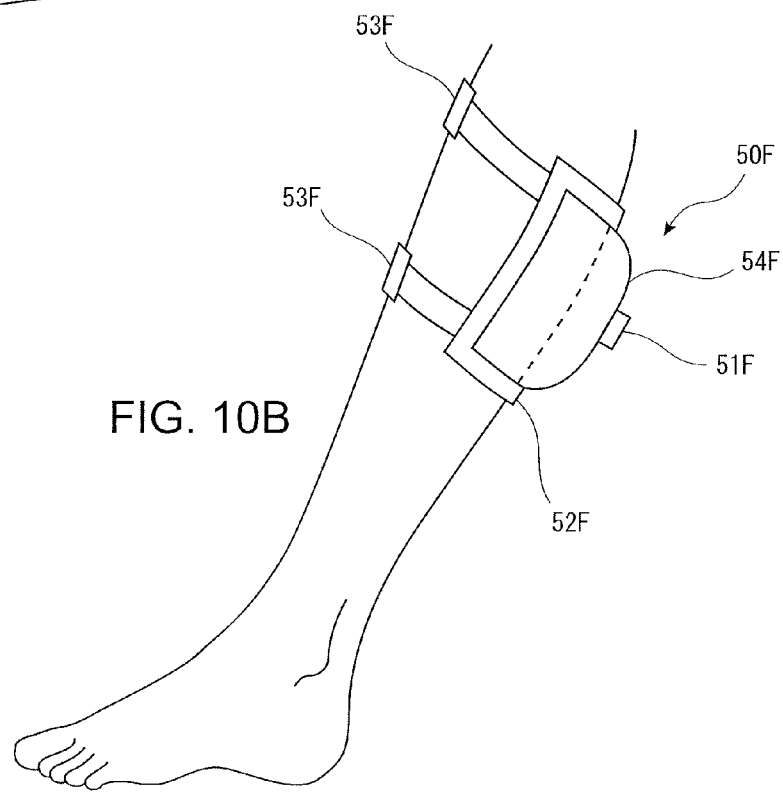

FIGS. 10A-10B show an example of a patch shaped pressurized bathing cover 50F. FIG. 10A is a view showing the outline of the patch shaped pressurized bathing cover 50F. FIG. 10B is a view showing an external appearance when attaching the patch shaped pressurized bathing cover 50F to the living organism (herein, the lower extremity). The pressurized bathing cover 50F is composed of a cover part 54F for covering the skin and mucous membrane of the living organism, a stopper 52F provided at the margin of the cover part 54F and directly attached to the skin and mucous membrane, fasteners 53F made of belts or strings for fastening the cover part 54F to the living organism, and a supply port 51F for supplying the gas mist into the space defined by the cover 54D and the stopper 52F.

In regard to the pressurized living organism bathing cover 50, various shapes may be assumed other than the examples shown in FIGS. 8 to 10. In particular, since this invention can be applied to not only the human living organism, but also to general kinds of animals, the pressurized living organism bathing cover 50 adopts shapes in view of the using objects and using parts. In sum, if forming spaces for sealing skins and mucous membranes of living organism, and enabling to form inside spaces for sealing the gas mist, any shapes are sufficient. Although omitting illustrations here, it is suitable to furnish air ports for discharging the gas mist in the pressurized living organism bathing cover 50, or controlling pressurization.

In the pressurized gas mist bathing, the gas mist is contacted to the skin and mucous membrane of the living organism at pressure of more than the predetermined value, and heightens the effects by pulsing at predetermined intervals, and therefore the control device 60 may supply the gas mist into the pressurized living organism bathing cover 50 intermittently at fixed rhythm. As to the interval pressurization at such a case, if synchronizing with pulsations, the effects are more heightened.

[Second Embodiment]

Figure 11:
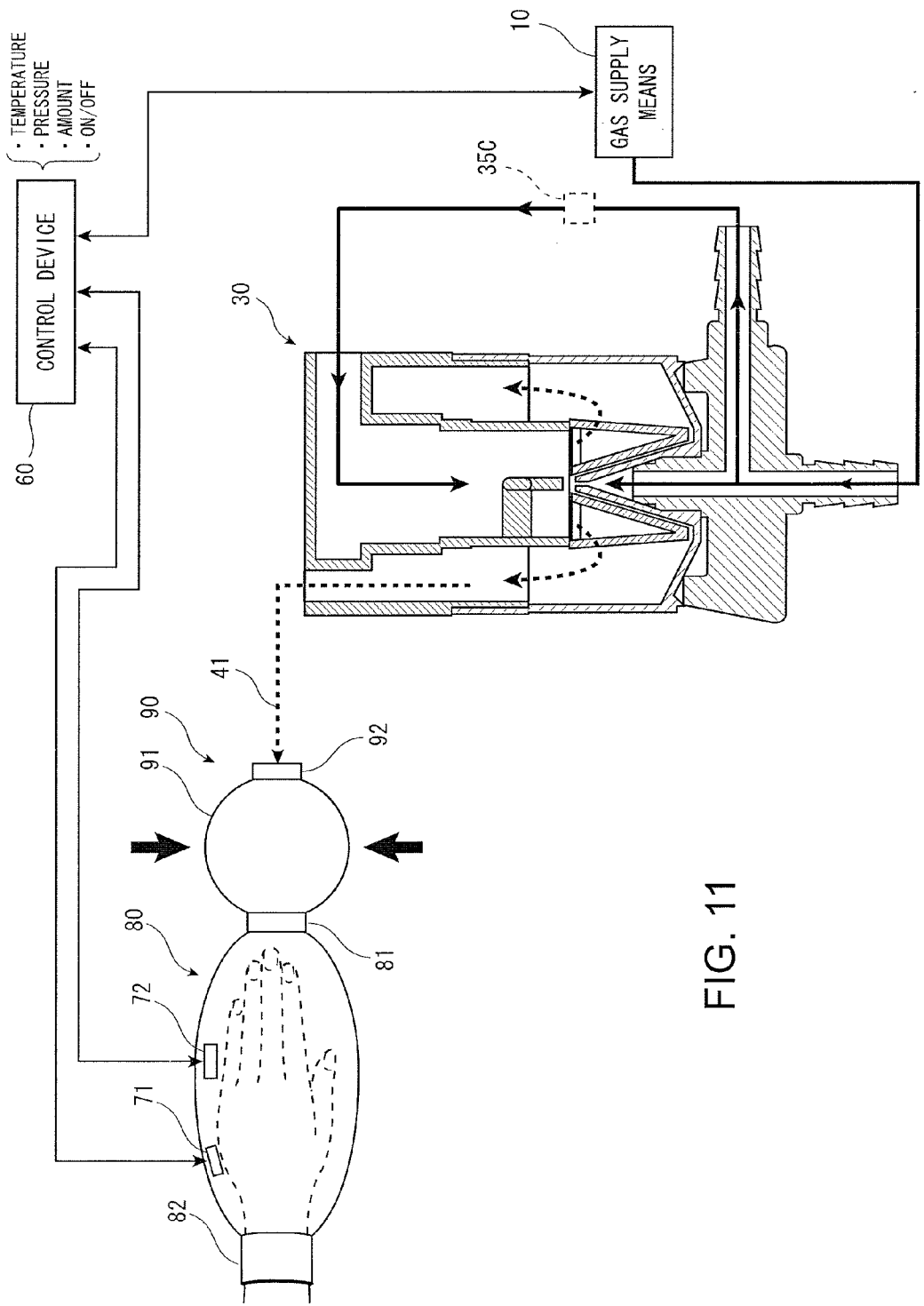

FIG. 11 is the generally schematic view of the pressurized gas mist bathing system in dependence on a second embodiment of this invention. This embodiment will explain the pressurized gas mist bathing system further having a pressurizing means for simplifying pressurization within the pressurized living organism bathing cover. As to the same parts as those of the first embodiment shown in FIG. 1, the same numerals will be given, and detailed explanation will be omitted.

As shown in FIG. 11, the pressurized gas mist bathing system of this embodiment has a pressurized living organism bathing cover 80 forming a space into which the gas mist and gas are sealed, and a pressurizing means 90 connecting the pressurized bathing cover 80 for carrying out pressurization therein.

The pressurized gas mist bathing cover 80 has almost the same structure of the pressurized living organism bathing cover 50 shown in the first embodiment, and has a gas mist supply port 81 and a stopper gas 82, providing that the supply port 81 is connected to the pressurizing means 90 in the present embodiment. By the way, as an example herein, the pressurized bathing cover 80 having a shape of covering a hand of the living organism is illustrated.

The pressurizing means 90 pressurizes the inside of the pressurized living organism bathing cover 80, and therefore has a hollow gas storage 91 communicating with the pressurized living organism bathing cover 80. The gas storage 91 is composed of a soft material having pressure resistance, non-air permeability and non-moisture permeability. The pressurizing means 90 is connected to the supply port 81 of the living organism pressurized bathing cover 80, and has a supply port 92 from which the gas mist is supplied into the gas storage 91. In addition, the supply port 92 of the pressurizing means 90 is also provided inside with the check valve for checking backflow of the gas mist.

For pressurizing the pressurized living organism bathing cover 80 by the pressurizing means 90, the gas mist is stored in the gas storage 91 under a condition where the gas mist is moderately stored within the pressurized living organism bathing cover 80. If pressurizing the gas storage 91 in a manner as crashing as shown with arrows in FIG. 11, the gas mist in the gas storage 91 is exhausted into the pressurized living organism bathing cover 80, so that the inside of the pressurized living organism bathing cover 80 can be pressurized.

The pressurizing means 90 is enough with a structure of manually pushing, or sufficient to mechanically control by the control device 60 using a driving device. As mentioned above, since pressurization in the pressurized gas mist bath heightens effects by pulse-like performance of a determined interval, it is effective to intermittently push the pressurizing means 90 at constant rhythm.

When taking the pressurized gas mist bathing by use of the pressurized gas mist bathing system of this embodiment, at first, the sealed generator main body 31 is opened, the gas supply means connecting portion 35 and the cover 36 are set, so that the gas mist generator 30 is accomplished. Next, the gas supply means 10, the gas mist generator 30, the pressurized living organism bathing cover 80, the control device 60 and others are connected successively. The pressurized living organism bathing cover 80 is fixed to the living organism (herein, the hand) and closed. Supply of gas starts from the gas supply means 10 into the gas mist generator 30 for generating the gas mist. During this period, the control device 60 controls supply pressure, amount of the liquid and gas, and temperature.

The generated gas mist is discharged from the gas mist outlet 39 into the pressurizing means 90 and the pressurized living organism bathing cover 80 through gas mist pipe 41. The control device 60 controls the respective means from measuring values of the temperature gauge 72, such that the inside of the pressurized living organism bathing cover 80 is maintained under the optimum heated condition (for example, around 38° C.). When the gas mist of the optimum amount is stored in the pressurized living organism bathing cover 80 and the pressurizing means 90, the pressurizing means 90 is pushed to moderately pressurize (around 1.02 to 2.5 air pressure) the pressurized living organism bathing cover 80 for taking the gas mist pressurizing bathing.

As having mentioned in the first embodiment, various shapes of the pressurized living organism bathing covers 80 maybe employed, since they are applied to many parts of the living organism, providing that in the present embodiment, the pressurized living organism bathing cover 80 must have a site easily pressurized by the pressuring means 90. For example, when manually pressurizing the pressuring means 90, the pressuring means 90 must have such a size grasped by man's both hands, and the pressurized living organism bathing cover 80 pressurized with the pressuring means 90 is also limited in size, accordingly. Further, even if, in a case of pressurizing with such as a driving device, the pressuring means 90 and also a means pressurizing this means are desirably compact not to actually keep wide places, therefore, the present embodiment is applicable to the pressurized living organism bathing cover 80 which is comparatively compact (covering local parts of the living organism).

Figure 12A:
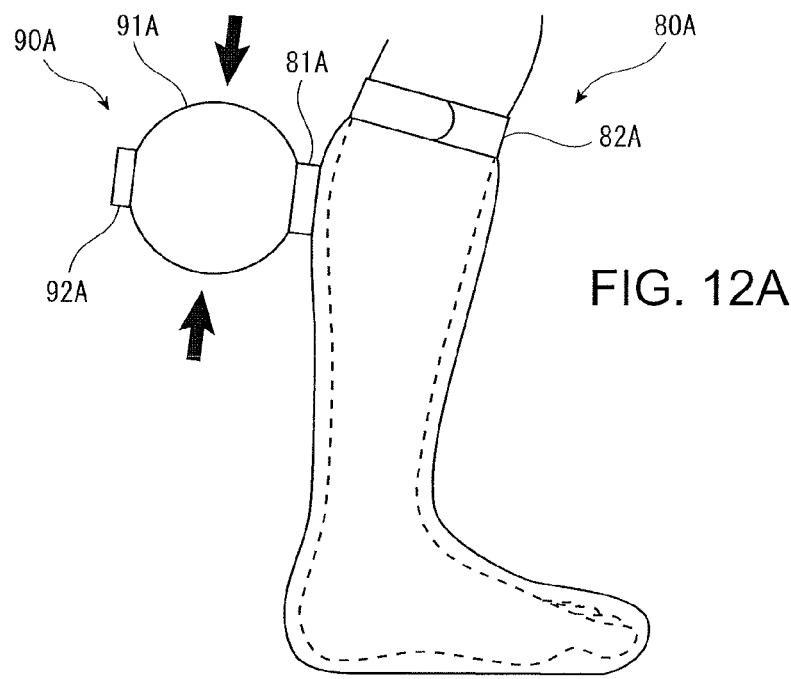
Figure 12B:
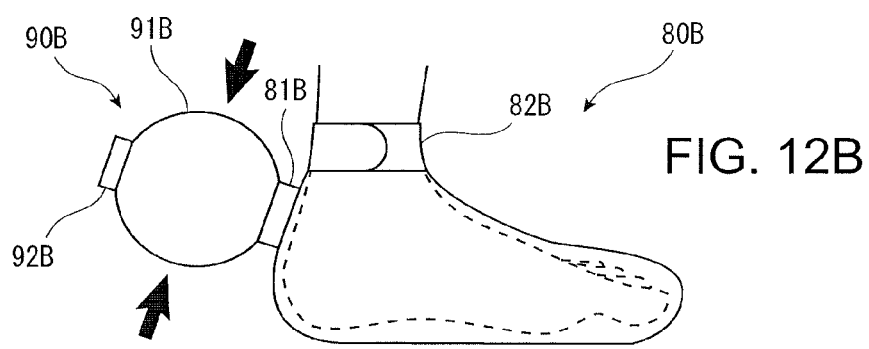
Figure 12C:
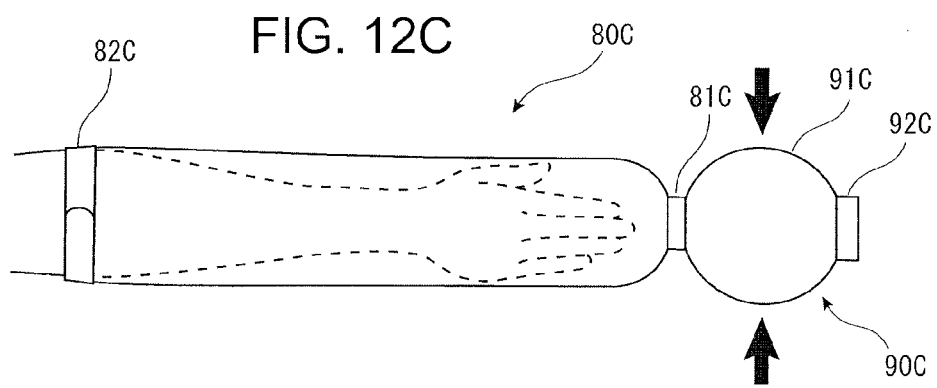

FIGS. 12 and 13 show the examples of shapes of the pressurized living organism bathing cover 80 to which the present embodiment is easily applied as well as those of the pressuring means 90 connected thereto. FIG. 12A is a pressurized living organism bathing cover 80A for one-side lower extremity (lower part under a knee) of the living organism. The pressurized bathing cover 80A has a supply port 81A for introducing inside the gas mist, and the stopper 82A at its open. The supply port 81A is connected to a pressuring means 90A. The pressuring means 90A has a gas storage 91A and a supply port 92A. FIG. 12B is a pressurized living organism bathing cover 80B for feet. The pressurized bathing cover 80B has a supply port 81B for introducing inside the gas mist and a stopper 82B at its opening part. The supply port 81B is connected with a pressurizing means 90B. The pressurizing means 90B has a gas storage 91B and a supply port 92B. FIG. 120 is a pressurized living organism bathing cover 80C for a forearm. The pressurized bathing cover 80C has a supply port 81C for introducing inside the gas mist and a stopper 82C at its opening part. The supply port 81C is connected with a pressurizing means 90C. The pressurizing means 90C has a gas storage 91B and a supply port 92C.

Figure 13A:
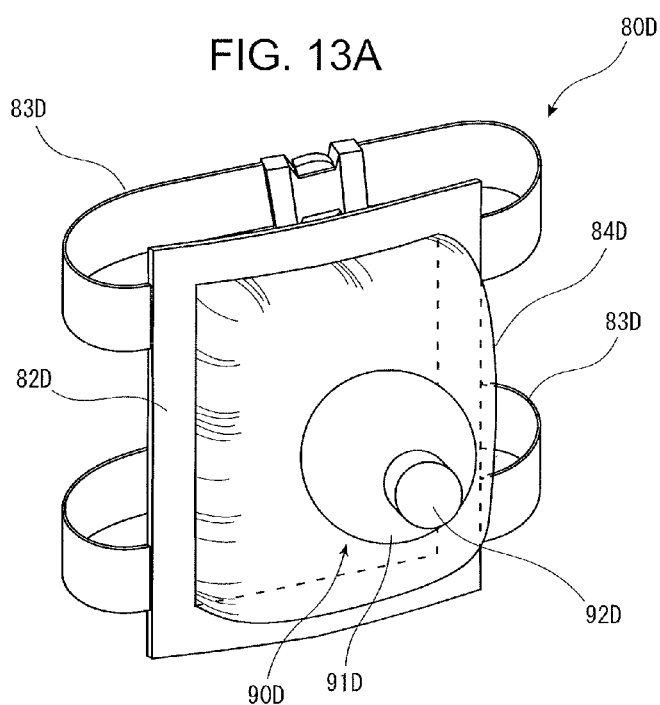
Figure 13B:
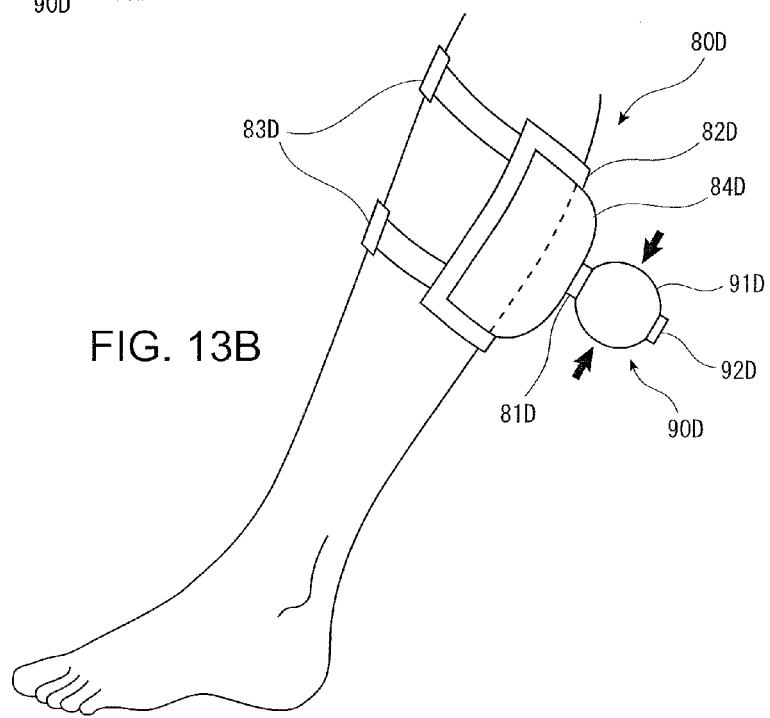

FIGS. 13A-13B show a patch shaped pressurized living organism living organism bathing cover 80D. FIG. 13A is a view showing the outline of the patch shaped bathing cover 80D. FIG. 13B is a view showing an external appearance when attaching the patch shaped pressurized bathing cover 80D to the living organism (herein, the lower extremity). The pressurized bathing cover 80D is composed of a cover part 84D for covering the skin and mucous membrane of the living organism, a stopper 82D provided at the margin of the cover part 84D and directly attached to the skin and mucous membrane of the living organism, fasteners 83D made of belts or strings for fastening the cover part 84D to the living organism, and a supply port 81D for supplying the gas mist into the space defined by the cover 84D and the stopper 82D. The supply port 81D is connected with the pressurizing means 90D. The pressurizing means 90D has the gas storage 91D and the supply port 92D.

Incidentally, although having not shown here, preferably there is provided an exhaust port for exhausting the gas mist in the living organism pressurized bathing cover 80 or adjusting pressure.

In the above embodiment, the pressurizing means 90 is composed of a hollow gas storage 91 communicating to the pressurized living organism bathing cover 80, and any members are sufficient if enabling to conveniently pressurize the pressurized living organism bathing cover 80 such as a member compressing to crash the pressurized living organism bathing cover 80 from an outer periphery.

[Third Embodiment]

Figure 14:
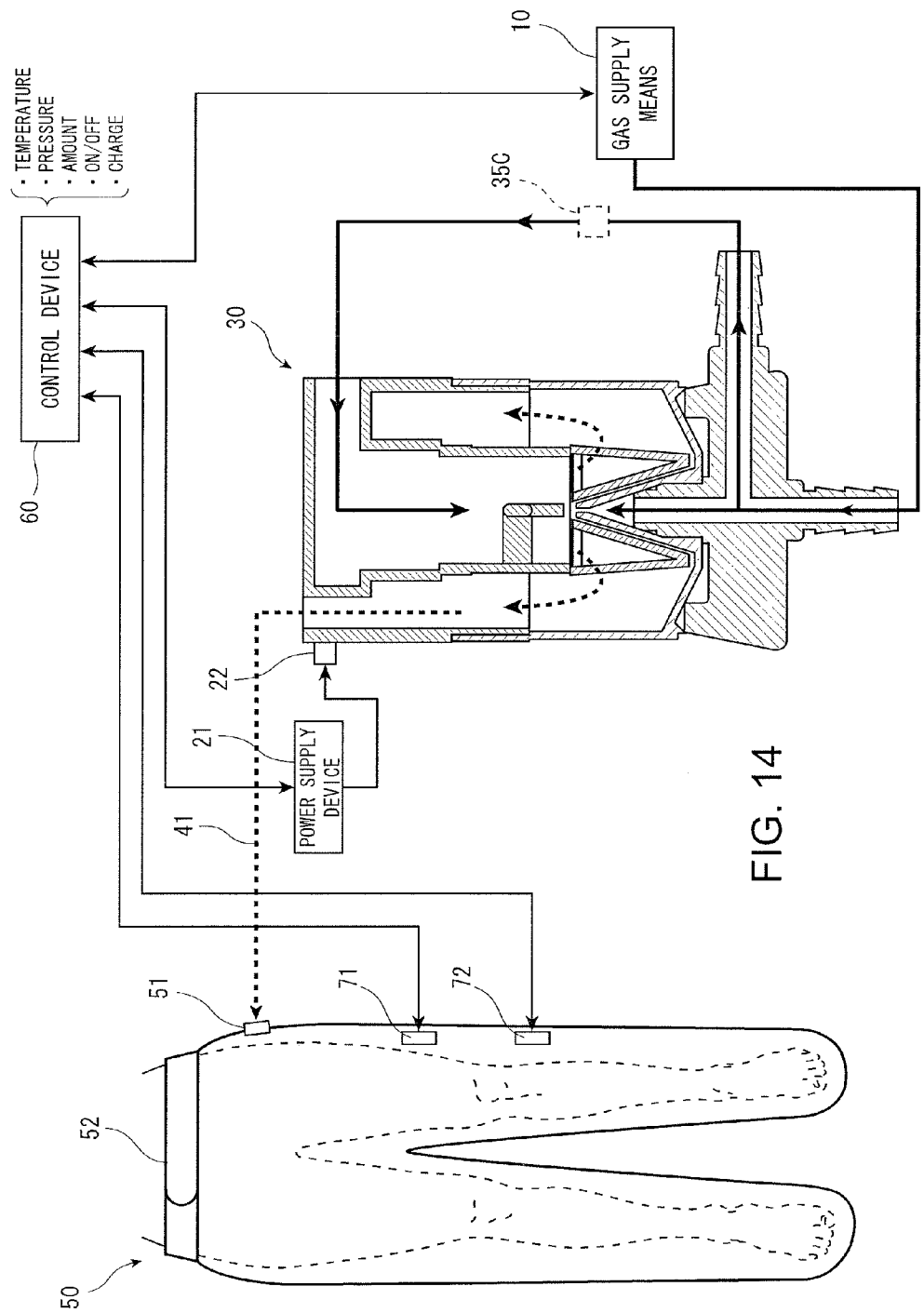

FIG. 14 is the generally schematic view of the pressurized gas mist bathing system depending on the third embodiment of this invention. This embodiment will explain the pressurized gas mist bathing system further having a means for electrically charging a generated mist. As to the same parts as those of the first embodiment shown in FIG. 1, the same numerals will be given, and detailed explanation will be omitted.

As shown in FIG. 14, a pressurized gas mist bathing system of this embodiment is arranged with an electrode 22 in the vicinity of an exit of a gas mist outlet 39A of a gas mist generator 30. The electrode 22 is connected to a source device 21, and a control device 60 sets voltage values and performs on-off control.

The electrode 22 supplies an electric charge (-charge is desirable) when exhausting the mist generated by the gas mist generator 30. Thereby, the mist is made charged so that adhesion to a charged material can be heightened. That is, if heightening adhesion to the skin and the mucous membrane of the living organism, an effect of more increasing absorption rate of gas by the pressurized gas mist bathing is further heightened, and if the gas mist contains the above mentioned medicines, penetration into the skin and the mucous membrane can be accelerated.

For carrying out the gas mist pressurized bathing by using the pressurized gas mist bathing system of the present embodiment, at first, the sealed generator main body 31 is opened, and the gas supply means connecting portion 35 and the cover 36 are set to accomplish the gas mist generator 30. Subsequently, the gas supply means 10, the gas mist generator 30, the pressurized living organism bathing cover 50, the control device 60 and so on are connected, respectively. The pressurized living organism bathing cover 50 is fixedly secured to the living organism (herein, the lower extremity) and closed. During this period, the control device 60 controls supply pressure, amount of the liquid, gas or temperature. Further, the control device 60 turns on the power supply device 21 and gives an electric charge to the mist from the electrode 22.

The generated gas mist is discharged from the gas mist outlet 39 into the pressurized living organism bathing cover 50 through the gas mist supply pipe 41. The control device 60 controls each of the means from measuring values of the manometer 71 and the temperature gauge 72 such that the inside of the pressurized living organism bathing cover 50 becomes the optimum pressurized and heated conditions (around 1.02 to 2.5 air pressure and around 38° C.), and under this condition the gas mist pressure bathing is carried out.

Having composed the structure as mentioned above, according to the pressurized gas mist bathing system, in the gas mist generating means, the liquid storage is made displaceable with another liquid storage, whereby attention is given to hygiene as well as cost reduction is realized.

The above references have explained the embodiments of the invention, but are not limited thereto, and so far as not deviating from the subject matter of the invention, various kinds of embodiments are, of course, available.

INDUSTRIAL APPLICABILITY

The present invention relates to the pressurized gas mist bathing system for improving absorption efficiency of gas from the skin or the mucous membrane of the living organism, in which the mist is prepared by pulverizing and dissolving the liquid of oxygen or carbon dioxide and a medicine, or a mixed gas of oxygen and carbon dioxide and the medicine, and the mist is caused to directly contact the skin and mucous membrane of the living organism at pressure of not less than a predetermined value accompanying industrial applicability.

EXPLANATION OF THE REFERENCE NUMERALS AND SIGNS

10: gas supply means
21: power supply device
22: electrode
30: gas mist generator
31: generator main body
31A, 31B: plug
31C: film
32: liquid storage
33: nozzle
33A: point open
34: liquid suction pipe forming member
34A: liquid suction pipe
34B: point end
35: gas supply means connecting portion
35A: gas discharge port
35B: branch part
35C: flow controller
36: cover
37: gas inlet
38: baffle
38A: baffle supporter
39: gas mist outlet
41: gas mist supply pipe
50, 50A, 50B, 50C, 50D, 50E, 50F: pressurized living organism bathing cover
51, 51A, 51B, 51C, 51D, 51E, 51F: supply port
52, 52A, 52B, 52C, 52D, 52E, 52F: stopper
53A: stopper
53F: fixing part
54F: cover
60: control device
71: manometer
72: temperature gauge
80, 80A, 80B, 80C, 80D: pressurized living organism bathing cover
81, 81A, 81B, 81C, 81D: supply port
82, 82A, 82B, 82C, 82D: stopper
83D: fixing part
84D: cover
90, 90A, 90B, 90C, 90D: pressurizing means
91, 91A, 91B, 91C, 91D: gas storage
92, 92A, 92B, 92C, 92D: supply port

The invention claimed is:

1. A pressurized gas mist bathing system, which causes a gas mist to contact a skin or a mucous membrane of a living organism, the gas mist having been prepared by pulverizing and dissolving carbon dioxide or oxygen and liquid, or a gas of carbon dioxide and oxygen and liquid with concentration not less than a predetermined value, the pressurized gas mist bathing system comprising:
- a gas supply;
- a gas mist generator, which has
  - a connecting portion connected to the gas supply,
  - a generator main body including
    - a liquid storage storing a liquid,
    - a nozzle having a tip opening, and discharging the gas supplied from the gas supply from the tip opening, and
    - a liquid suction pipe forming member covering the nozzle, and forming a liquid suction pipe sucking up the liquid stored in the liquid storage up to a front end of the nozzle,
  - a collision member colliding the liquid blown up by a gas stream from the nozzle therewith,
  - a cylindrical gas inlet supplied with the gas and leading the gas till an upper portion of the nozzle, and
  - a donut-shaped gas mist outlet collecting and discharging the gas mist; and
- a living organism cover for covering the skin or the mucous membrane of the living organism and formed with a space for sealing inside the gas mist from the gas mist generator, wherein the generator main body is displaceable from the gas mist generator and replaced by another generator main body.

2. The pressurized gas mist bathing system as set forth in claim 1, further comprising sensors for detecting measured values of air pressure, temperature, concentrations of oxygen and carbon dioxide, moisture and others in the living organism cover, and
- a control device for controlling an interior of the living organism cover based on the measured values of the sensors to be within ranges of set values having been previously determined.

3. The pressurized gas mist bathing system as set forth in claim 1, further comprising a pressurizing member for pressurizing an interior of the living organism cover.

4. The pressurized gas mist bathing system as set forth in claim 3, wherein the pressurizing member communicates with the living organism cover, and comprises a hollow gas storage enabling to discharge the gas mist into the living organism cover.

5. The pressurized gas mist bathing system as set forth in claim 2, wherein the gas mist is supplied intermittently into the living organism cover by the control device, whereby the living organism cover is effected with interval pressurization.

6. The pressurized gas mist bathing system as set forth in claim 4, wherein the pressurizing member intermittently discharges the gas mist into the living organism cover, thereby to carry out interval pressurization on the living organism cover.

7. The pressurized gas mist bathing system as set forth in claim 1, wherein the gas mist generator has an air hole for taking in outside air.

8. The pressurized gas mist bathing system as set forth in claim 1, wherein the liquid is any one or plural combination of water, ionic water, ozone water, physiological salt solution, purified water, or sterilized and purified water.

9. The pressurized gas mist bathing system as set forth in claim 8, wherein the liquid contains any one or plural combination of menthol, vitamin E, vitamin C derivative, retinol, anesthetic agent, cyclodextrin, photo catalyst, complex of photo catalyst and apatite, hyaluronic acid, coenzyme Q10, seed oil, propolis, ethanol, chlorhexidine gluconate, amphoteric surface active agent, benzalkonium chloride, alkyl diamino etherglycine acetate, sodium hypo-chlorite, peracetic acid, sodium sesquicarbonate, silica, povidone-iodine, sodium hydrogen carbonate, carbonate spring agent of high concentration, anti-allergic agent, anti-inflammatory agent, anti-febrile agent, anti-fungus agent, anti-influenza virus agent, influenza vaccine, steroid agent, anti-cancer agent, anti-hypertensive agent, cosmetic, or trichogen.

10. The pressurized gas mist bathing system as set forth in claim 1, wherein a size of the mist supplied from the gas mist generator into the living organism cover is not larger than 10 µm.

11. The pressurized gas mist bathing system as set forth in claim 2, wherein the control device holds pressure at 1.02 to 2.5 air pressure within the living organism cover when taking pressurized gas mist bath.

12. The pressurized gas mist bathing system as set forth in claim 1, further comprising an electric charge supply device for supplying charge to the mist from the gas mist generator.

13. The pressurized gas mist bathing system as set forth in claim 12, wherein the charge is minus charge.

14. The pressurized gas mist bathing system as set forth in claim 1, wherein the gas mist generator has a gas mist supply pipe for supplying the gas mist into the living organism cover, and the gas mist supply pipe has a filter for removing liquid drops attaching to an inside of the pipe.

15. The pressurized gas mist bathing system as set forth in claim 1, wherein the gas mist generator has a gas mist supply pipe for supplying the gas mist into the living organism cover, and the gas mist supply pipe has a cornice shaped pipe over a whole or at one part of the gas mist supply pipe.

16. The pressurized gas mist bathing system as set forth in claim 1, wherein the gas mist generator has a gas mist supply pipe for supplying the gas mist into the living organism cover, and the gas mist supply pipe is provided with a check valve.

17. The pressurized gas mist bathing system as set forth in claim 1, wherein the living organism cover has a gas mist supply port, and the gas supply port has a check valve.

18. The pressurized gas mist bathing system as set forth in claim 1, wherein the control device stops gas supply from the gas supply when a pressure value becomes more than a predetermined value.

19. The pressurized gas mist bathing system as set forth in claim 1, wherein the generator main body is in advance sterilized.

* * * * *